(12) United States Patent
Loney et al.

(10) Patent No.: US 7,148,492 B2
(45) Date of Patent: Dec. 12, 2006

(54) SYSTEM, METHOD, AND PRODUCT FOR PROVIDING A WAVELENGTH TUNABLE EXCITATION BEAM

(75) Inventors: Gregory C. Loney, Concord, MA (US); Nathan K. Weiner, Upton, MA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 10/846,261

(22) Filed: May 13, 2004

(65) Prior Publication Data

US 2005/0001176 A1 Jan. 6, 2005

Related U.S. Application Data

(60) Provisional application No. 60/469,926, filed on May 13, 2003.

(51) Int. Cl.
*G01N 21/64* (2006.01)

(52) U.S. Cl. .............................. 250/458.1; 250/459.1; 250/461.2

(58) Field of Classification Search ............. 250/458.1, 250/459.1, 461.2, 483.1, 559.05, 559.06; 356/317, 318, 417
See application file for complete search history.

(56) References Cited

U.S. PATENT DOCUMENTS

| | | | |
|---|---|---|---|
| 5,591,981 A * | 1/1997 | Heffelfinger et al. .... | 250/458.1 |
| 6,617,590 B1 | 9/2003 | Nishioka et al. | |
| 6,754,249 B1 | 6/2004 | Missey et al. | |
| 6,991,927 B1 | 1/2006 | Mross et al. | |
| 2001/0041843 A1* | 11/2001 | Modell et al. .............. | 600/473 |
| 2001/0055764 A1* | 12/2001 | Empedocles et al. .......... | 435/6 |
| 2002/0024026 A1* | 2/2002 | Kaushikkar ............ | 250/559.06 |
| 2002/0159057 A1* | 10/2002 | Odoy et al. ................. | 356/318 |
| 2002/0168094 A1* | 11/2002 | Kaushikkar et al. ........ | 382/128 |
| 2003/0222222 A1 | 12/2003 | Dong et al. | |
| 2004/0223881 A1 | 11/2004 | Cunningham et al. | |
| 2004/0239944 A1 | 12/2004 | Shiral et al. | |

OTHER PUBLICATIONS

PCT International Search Report and Written Opinion, Sep. 14, 2005.

* cited by examiner

*Primary Examiner*—David Porta
*Assistant Examiner*—Faye Boosalis
(74) *Attorney, Agent, or Firm*—Jagtiani + Guttag

(57) ABSTRACT

A method for scanning a probe array is described. The method comprises tuning an excitation light to a plurality of wavelengths each within an excitation range of a fluorescent label associated with one or more target molecules; and directing the tuned excitation light of each wavelength at the probe array.

18 Claims, 4 Drawing Sheets

SYSTEM, METHOD, AND PRODUCT FOR PROVIDING A WAVELENGTH TUNABLE EXCITATION BEAM

RELATED APPLICATIONS

The present application claims priority to U.S. Provisional Patent Application Ser. No. 60/469,926, titled "System, Method, and Product for Multiple Wavelength Tunable Excitation Beam in a Microarray Scanner", filed May 13, 2003, which is hereby incorporated by reference herein in its entirety for all purposes.

BACKGROUND

1. Field of the Invention

The present invention relates generally to the examination of biological materials and, more particularly to providing a wavelength-tunable excitation light to excite a plurality of fluorophores associated with biological probe arrays and detect emissions from each of the fluorophores in response to the excitation light.

2. Related Art

Synthesized nucleic acid probe arrays, such as Affymetrix® GeneChip® probe arrays, and spotted probe arrays, have been used to generate unprecedented amounts of information about biological systems. For example, the GeneChip® Human Genome U133 Plus 2.0 probe array available from Affymetrix, Inc. of Santa Clara, Calif., is comprised of a single microarray containing over 1,000,000 unique oligonucleotide features covering more than 47,000 transcripts that represent more than 33,000 human genes. Analysis of expression data from such microarrays may lead to the development of new drugs and new diagnostic tools.

SUMMARY OF THE INVENTION

Systems, methods, and products to address these and other needs are described herein with respect to illustrative, non-limiting, implementations. Various alternatives, modifications and equivalents are possible. For example, certain systems, methods, and computer software products are described herein using exemplary implementations for analyzing data from arrays of biological materials produced by the Affymetrix® 417™ or 427™ Arrayer. Other illustrative implementations are referred to in relation to data from Affymetrix® GeneChip® probe arrays. However, these systems, methods, and products may be applied with respect to many other types of probe arrays and, more generally, with respect to numerous parallel biological assays produced in accordance with other conventional technologies and/or produced in accordance with techniques that may be developed in the future. For example, the systems, methods, and products described herein may be applied to parallel assays of nucleic acids, PCR products generated from cDNA clones, proteins, antibodies, or many other biological materials. These materials may be disposed on slides (as typically used for spotted arrays), on substrates employed for GeneChip® arrays, or on beads, optical fibers, or other substrates or media, which may include polymeric coatings or other layers on top of slides or other substrates. Moreover, the probes need not be immobilized in or on a substrate, and, if immobilized, need not be disposed in regular patterns or arrays. For convenience, the term "probe array" will generally be used broadly hereafter to refer to all of these types of arrays and parallel biological assays.

In one embodiment, a system for scanning biological probe arrays is described. The system comprises a biological probe array that comprises a plurality of probes disposed thereon, wherein one or more first probes is associated with a first label and one or more second probes is associated with a second label; and a source to provide light of a first wavelength and a second wavelength, wherein the first wavelength is within an excitation range of the first label and the second wavelength is within an excitation range of the second label.

Also, a method for scanning a probe array is described. The method comprises tuning an excitation light to a plurality of wavelengths each within an excitation range of a fluorescent label associated with one or more target molecules; and directing the tuned excitation light of each wavelength at the probe array.

Furthermore, a system for providing multiple wavelengths of light to a probe array is described. The system comprises a means for tuning an excitation light to a plurality of wavelengths each within an excitation range of a fluorescent label associated with one or more target molecules; a means for directing the tuned excitation light of each wavelength at the probe array; and a detector to detect each a second wavelength of light, wherein the second wavelength is emitted in response to the first wavelength.

Additionally, a system for directing multiple wavelengths of light to a probe array and detection of emitted light is described. The system comprises a scanner to tune an excitation light to a plurality of wavelengths each within an excitation range of a fluorescent label associated with one or more target molecules, and detect each a second wavelength of light, wherein the second wavelength is emitted in response to the first wavelength.

The above embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

BRIEF DESCRIPTION OF THE DRAWINGS

The above and further features will be more clearly appreciated from the following detailed description when taken in conjunction with the accompanying drawings. In the drawings, like reference numerals indicate like structures or method steps and the leftmost digit of a reference numeral indicates the number of the figure in which the referenced element first appears (for example, the element 100 appears first in FIG. 1). In functional block diagrams, rectangles generally indicate functional elements and parallelograms generally indicate data. In method flow charts, rectangles generally indicate method steps and diamond shapes generally indicate decision elements. All of these conventions, however, are intended to be typical or illustrative, rather than limiting.

DETAILED DESCRIPTION a) General

Figure 1:
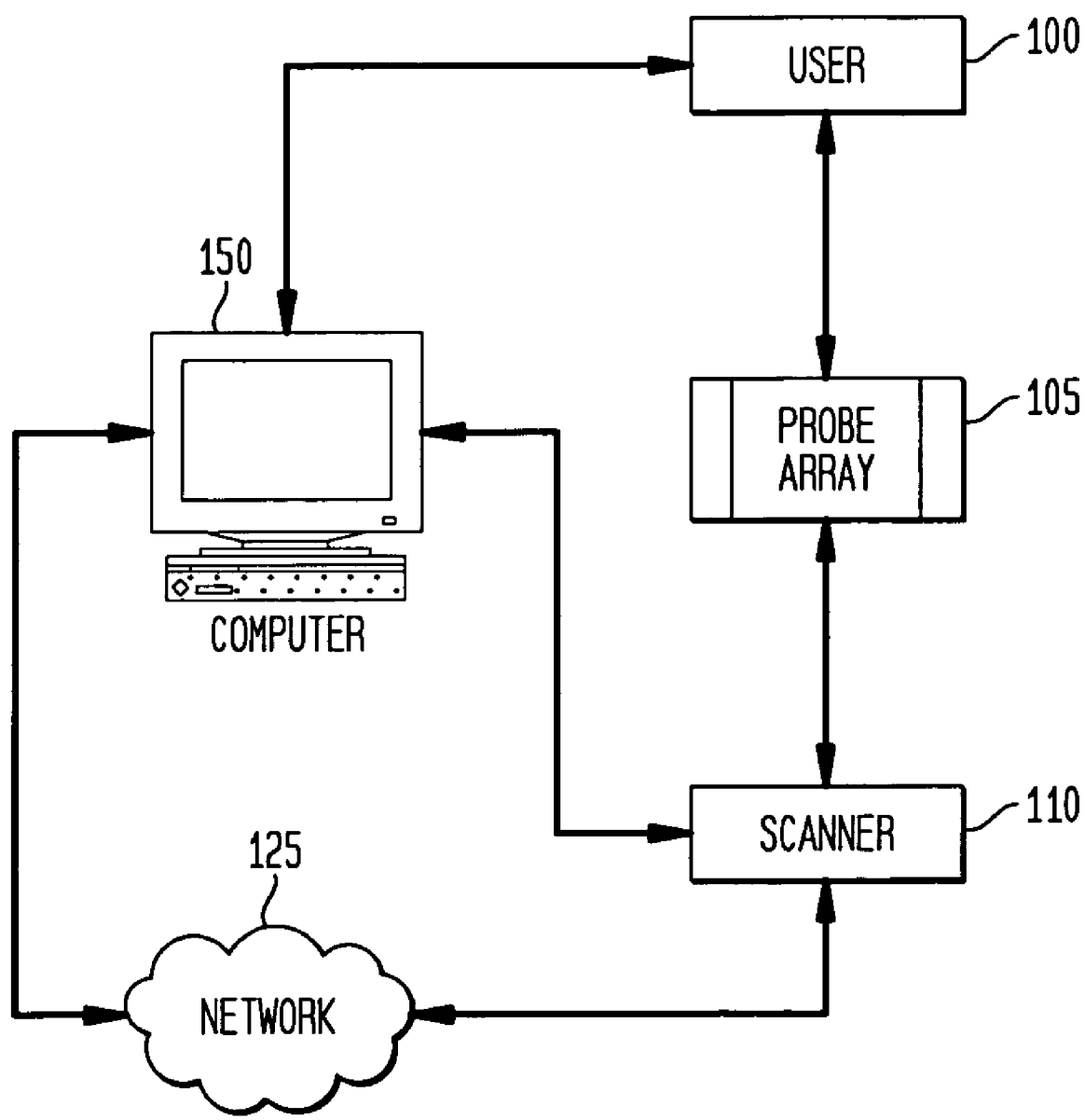
FIG. 1 is a functional block diagram of one embodiment of a computer system and a scanner instrument.

The present invention has many embodiments and the following description relies on various patents, applications and other references for details known to those of the art. Therefore, when a patent, application, or other reference is cited or otherwise referenced below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (*Vols. I–IV*), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, N.Y. Gait, "*Oligonucleotide Synthesis: A Practical Approach*" 1984, *IRL Press, London*, Nelson and Cox (2000), *Lehninger, Principles of Biochemistry* 3$^{rd}$ Ed., W. H. Freeman Pub., New York, N.Y. and Berg et al. (2002) *Biochemistry*, 5$^{th}$ Ed., W. H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 0.5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285 (International Publication Number WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. Patent Application Publication 20030036069), and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, e.g., *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159, 4,965,188, and 5,333,675, and each of which is incorporated herein by reference in their entireties for all purposes. The sample may be amplified on the array. See, for example, U.S. Pat. No. 6,300,070 and U.S. Ser. No. 09/513,300, which are incorporated herein by reference.

Other suitable amplification methods include the ligase chain reaction (LCR) (e.g., Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA,* 87, 1874 (1990) and WO90/06995), selective amplification of target polynucleotide sequences (U.S. Pat. No. 6,410,276), consensus sequence primed polymerase chain reaction (CP- PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. Ser. Nos. 09/916,135, 09/920,491 (U.S. Patent Application Publication 20030096235), 09/910,292 (U.S. Patent Application Publication 20030082543), and Ser. No. 10/013,598.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* ($2^{nd}$ Ed. Cold Spring Harbor, N.Y, 1989); Berger and Kimmel *Methods in Enzymology*, Vol. 152, Guide to Molecular Cloning Techniques (Academic Press, Inc., San Diego, Calif., 1987); Young and Davism, *P.N.A.S*, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Ser. Nos. 10/389,194, 60/493,495 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have embodiments that include methods for providing genetic information over networks such as the Internet as shown in U.S. Ser. Nos. 10/197,621, 10/063,559 (United States Publication No. 20020183936), Ser. Nos. 10/065,856, 10/065,868, 10/328,818, 10/328,872, 10/423,403, and 60/482,389.

b) Definitions

An "array" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports.

Nucleic acid library or array is an intentionally created collection of nucleic acids which can be prepared either synthetically or biosynthetically and screened for biological activity in a variety of different formats (e.g., libraries of soluble molecules; and libraries of oligos tethered to resin beads, silica chips, or other solid supports). Additionally, the term "array" is meant to include those libraries of nucleic acids which can be prepared by spotting nucleic acids of essentially any length (e.g., from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

Biopolymer or biological polymer: is intended to mean repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above. "Biopolymer synthesis" is intended to encompass the synthetic production, both organic and inorganic, of a biopolymer.

Related to a bioploymer is a "biomonomer" which is intended to mean a single unit of biopolymer, or a single unit which is not part of a biopolymer. Thus, for example, a nucleotide is a biomonomer within an oligonucleotide biopolymer, and an amino acid is a biomonomer within a protein or peptide biopolymer; avidin, biotin, antibodies, antibody fragments, etc., for example, are also biomonomers initiation Biomonomer: or "initiator biomonomer" is meant to indicate the first biomonomer which is covalently attached via reactive nucleophiles to the surface of the polymer, or the first biomonomer which is attached to a linker or spacer arm attached to the polymer, the linker or spacer arm being attached to the polymer via reactive nucleophiles.

Complementary: Refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

Combinatorial Synthesis Strategy: A combinatorial synthesis strategy is an ordered strategy for parallel synthesis of diverse polymer sequences by sequential addition of reagents which may be represented by a reactant matrix and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

Effective amount refers to an amount sufficient to induce a desired result.

Genome is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

Hybridization conditions will typically include salt concentrations of less than about 1 M, more usually less than about 500 mM and preferably less than about 200 mM. Hybridization temperatures can be as low as 5 degrees-Celsius (° C.), but are typically greater than 22° C., more typically greater than about 30° C., and preferably in excess of about 37° C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

Hybridizations, e.g., allele-specific probe hybridizations, are generally performed under stringent conditions. For example, conditions where the salt concentration is no more than about 1 Molar (M) and a temperature of at least 25° C., e.g., 750 mM NaCl, 50 mM NaPhosphate, 5 mM EDTA, pH 7.4 (5×SSPE) and a temperature of from about 25 to about 30° C.

Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25–30° C. are suitable for allele-specific probe hybridizations. For stringent conditions, see, for example, Sambrook, Fritsche and Maniatis. "Molecular Cloning A laboratory Manual" $2^{nd}$ Ed. Cold Spring Harbor Press (1989) which is hereby incorporated by reference in its entirety for all purposes above.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization."

Hybridization probes are oligonucleotides capable of binding in a base-specific manner to a complementary strand of nucleic acid. Such probes include peptide nucleic acids, as described in Nielsen et al., *Science* 254, 1497–1500 (1991), and other nucleic acid analogs and nucleic acid mimetics.

Hybridizing specifically to: refers to the binding, duplexing, or hybridizing of a molecule only to a particular nucleotide sequence or sequences under stringent conditions when that sequence is present in a complex mixture (e.g., total cellular) DNA or RNA.

Isolated nucleic acid is an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

Ligand: A ligand is a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (e.g., opiates, steroids, etc.), hormone receptors, peptides, enzymes, enzyme substrates, substrate analogs, transition state analogs, cofactors, drugs, proteins, and antibodies.

Linkage disequilibrium or allelic association means the preferential association of a particular allele or genetic marker with a specific allele, or genetic marker at a nearby chromosomal location more frequently than expected by chance for any particular allele frequency in the population. For example, if locus X has alleles a and b, which occur equally frequently, and linked locus Y has alleles c and d, which occur equally frequently, one would expect the combination of alleles a and c to occur with a frequency of 0.25. If alleles a and c occur more frequently, then alleles a and c are in linkage disequilibrium. Linkage disequilibrium may result from natural selection of certain combination of alleles or because an allele has been introduced into a population too recently to have reached equilibrium with linked alleles.

Mixed population or complex population: refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

Monomer: refers to any member of the set of molecules that can be joined together to form an oligomer or polymer. The set of monomers useful in the present invention includes, but is not restricted to, for the example of (poly) peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either subunit alone.

mRNA or mRNA transcripts: as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

Nucleic acid library or array is an intentionally created collection of nucleic acids which can be prepared either synthetically or biosynthetically and screened for biological activity in a variety of different formats (e.g., libraries of soluble molecules; and libraries of oligos tethered to resin beads, silica chips, or other solid supports). Additionally, the term "array" is meant to include those libraries of nucleic acids which can be prepared by spotting nucleic acids of essentially any length (e.g., from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

Nucleic acids according to the present invention may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793–800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

Probe: A probe is a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (e.g., opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

Primer is a single-stranded oligonucleotide capable of acting as a point of initiation for template-directed DNA synthesis under suitable conditions e.g., buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

Polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

Receptor: A molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to those molecules shown in U.S. Pat. No. 5,143,854, which is hereby incorporated by reference in its entirety.

"Solid support", "support", and "substrate" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

Target: A molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

c) Embodiments of the Present Invention

The description of various embodiments are presented below to provide examples of the presently described invention and are not intended to be limiting in any way. Also, reference will be made to articles and patents to show general features that are incorporated into the present disclosure, but the invention is not limited by these descriptions. Many scanner designs may be used in order to provide excitation light and detect emission signals appropriate for the acquisition of experimental data derived from probe array 105.

Probe Array 105: An illustrative example of probe array 105 is provided in FIG. 1. Descriptions of probe arrays are provided above with respect to "Nucleic Acid Probe arrays" and other related disclosure. In various implementations probe array 105 may be disposed in a cartridge or housing such as, for example, the GeneChip® probe array available from Affymetrix, Inc. of Santa Clara Calif.

Computer 150: An illustrative example of computer 150 is provided in FIG. 1 and also in greater detail in FIG. 2. Computer 150 may be any type of computer platform such as a workstation, a personal computer, a server, or any other present or future computer. Computer 150 typically includes known components such as a processor 255, an operating system 260, system memory 270, memory storage devices 281, and input-output controllers 275, and input/output devices 230. Input/Output Devices 230 may include display devices that provides visual information, this information typically may be logically and/or physically organized as an array of pixels. A Graphical user interface (GUI) controller may also be included that may comprise any of a variety of known or future software programs for providing graphical input and output interfaces to a user, such as user 110, and for processing user inputs.

It will be understood by those of ordinary skill in the relevant art that there are many possible configurations of the components of computer 150 and that some components that may typically be included in computer 150 are not shown, such as cache memory, a data backup unit, and many other devices. Processor 255 may be a commercially available processor such as an Itanium® or Pentium® processor made by Intel Corporation, a SPARC® processor made by Sun Microsystems, an Athalon™ or Opteron™ processor made by AMD corporation, or it may be one of other processors that are or will become available. Processor 255 executes operating system 260, which may be, for example, a Windows®-type operating system (such as Windows NT® 4.0 with SP6a, or Windows XP) from the Microsoft Corporation; a Unix® or Linux-type operating system available from many vendors or what is referred to as an open source; another or a future operating system; or some combination thereof. Operating system 260 interfaces with firmware and hardware in a well-known manner, and facilitates processor 255 in coordinating and executing the functions of various computer programs that may be written in a variety of programming languages. Operating system 260, typically in cooperation with processor 255, coordinates and executes functions of the other components of computer 150. Operating system 260 also provides scheduling, input-output control, file and data management, memory management, and communication control and related services, all in accordance with known techniques.

System memory 270 may be any of a variety of known or future memory storage devices. Examples include any commonly available random access memory (RAM), magnetic medium such as a resident hard disk or tape, an optical medium such as a read and write compact disc, or other memory storage device. Memory storage device 281 may be any of a variety of known or future devices, including a compact disk drive, a tape drive, a removable hard disk drive, or a diskette drive. Such types of memory storage device 281 typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory 270 and/or the program storage device used in conjunction with memory storage device 281.

In some embodiments, a computer program product is described comprising a computer usable medium having control logic (computer software program, including program code) stored therein. The control logic, when executed by processor 255, causes processor 255 to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers 275 could include any of a variety of known devices for accepting and processing information from a user, whether a human or a machine, whether local or remote. Such devices include, for example, modem cards, network interface cards, sound cards, or other types of controllers for any of a variety of known input devices. Output controllers of input-output controllers 275 could include controllers for any of a variety of known display devices for presenting information to a user, whether a human or a machine, whether local or remote. In the illustrated embodiment, the functional elements of computer 150 communicate with each other via system bus 290. Some of these communications may be accomplished in alternative embodiments using network or other types of remote communications.

Figure 2:
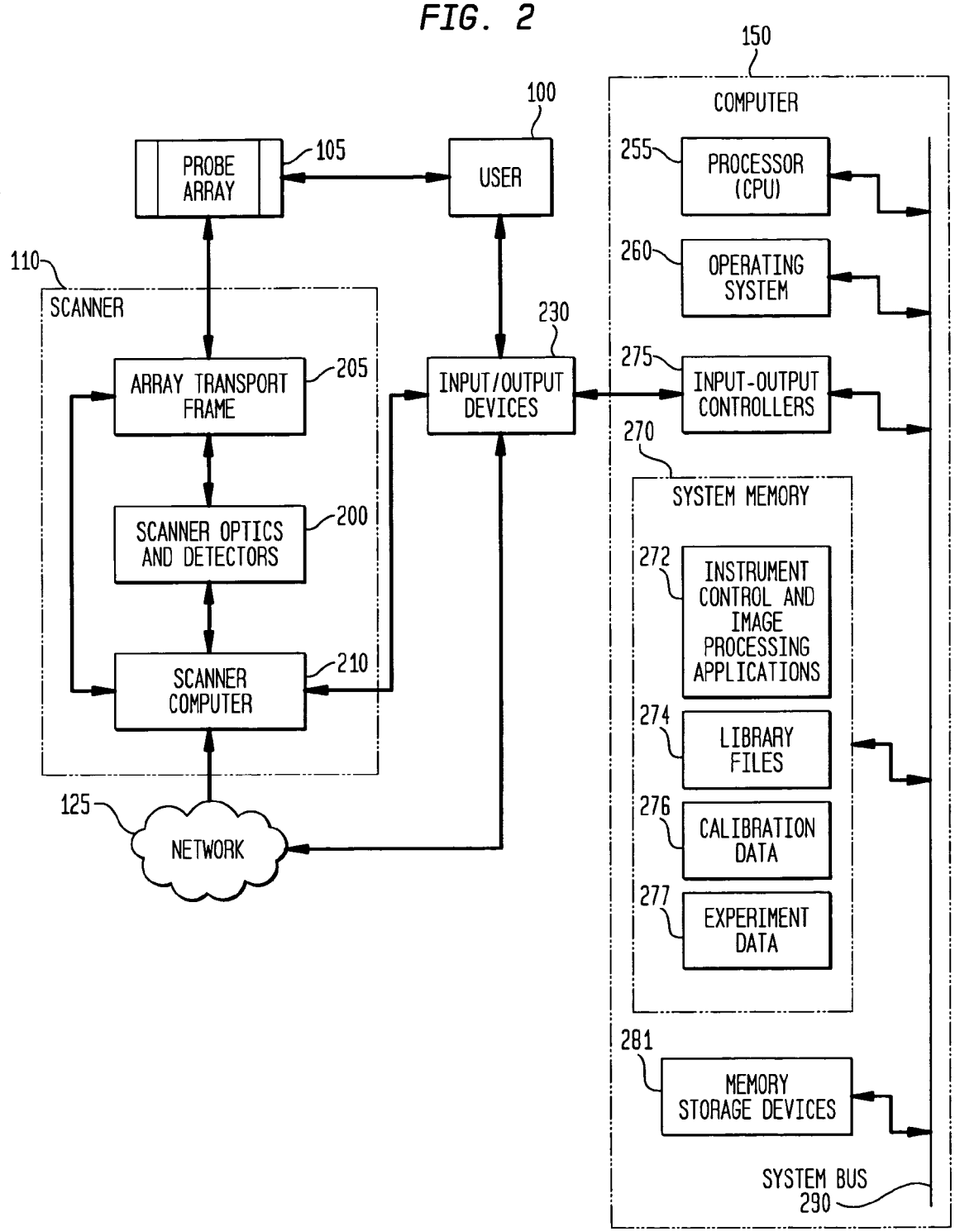
FIG. 2 is a functional block diagram of one embodiment of the computer and scanner of FIG. 1 including scanner optics and detectors.

As will be evident to those skilled in the relevant art, instrument control and image processing applications 272, if implemented in software, may be loaded into and executed from system memory 270 and/or memory storage device 281. All or portions of applications 272 may also reside in a read-only memory or similar device of memory storage device 281, such devices not requiring that applications/applications 272 first be loaded through input-output controllers 275. It will be understood by those skilled in the relevant art that applications 272, or portions of it, may be loaded by processor 255 in a known manner into system memory 270, or cache memory (not shown), or both, as advantageous for execution. Also illustrated in FIG. 2 are library files 274, calibration data 276, and experiment data 277 stored in system memory 270. For example, library files 274 could include data related to one or more probe arrays such as layout, content, or other related information. Also, calibration data 276 could include one or more values or other types of calibration data related to the calibration of scanner 110 or other instrument. Additionally, experiment data 277 could include data related to one or more experiments or assays such as the excitation ranges or values associated with one or more fluorescent labels.

In the example presented in FIG. 2, scanner computer 210 may include one or more components that are the same as or similar to those described above with respect to computer 150.

Network 125 may include one or more of the many various types of networks well known to those of ordinary skill in the art. For example, network 125 may include what is commonly referred to as a TCP/IP network, or other type of network that may include the internet, or intranet architectures.

Instrument control and image processing applications 272: Instrument control and image processing applications 272 may be any of a variety of known or future image processing applications. Examples of applications 272 include Affymetrix® Microarray Suite, Affymetrix® GeneChip® Operating Software (hereafter referred to as GCOS), and Affymetrix® Jaguar™ software, noted above. Applications 272 may be loaded into system memory 270 and/or memory storage device 281 through one of input devices 230.

Embodiments of applications 272 include executable code being stored in system memory 270 of an implementation of computer 150. Applications 272 may provide a single interface for both the client workstation and one or more servers such as, for instance, GeneChip® Operating Software Server (GCOS Server). Applications 272 could additionally provide the single user interface for one or more other workstations and/or one or more instruments. In the presently described implementation, the single interface may communicate with and control one or more elements of the one or more servers, one or more workstations, and the one or more instruments. In the described implementation the client workstation could be located locally or remotely to the one or more servers and/or one or more other workstations, and/or one or more instruments. The single interface may, in the present implementation, include an interactive graphical user interface that allows a user to make selections based upon information presented in the GUI. For example, applications 272 may provide an interactive GUI that allows a user to select from a variety of options including data selection, experiment parameters, calibration values, probe array information. Applications 272 may also provide a graphical representation of raw or processed image data (described further below) where the processed image data may also include annotation information superimposed upon the image such as, for instance, base calls, features of the probe array, or other useful annotation information. Further examples of providing annotation information on image data are provided in U.S. Provisional Patent Application Ser. No. 60/493,950, titled "System, Method, and Product for Displaying Annotation Information Associated with Microarray Image Data", filed Aug. 8, 2003, which is hereby incorporated by reference herein in its entirety for all purposes.

In alternative implementations, applications 272 may be executed on a server, or on one or more other computer platforms connected directly or indirectly (e.g., via another network, including the Internet or an Intranet) to network 125.

Embodiments of applications 272 also include instrument control features. The instrument control features may include the control of one or more elements of one or more instruments that could, for instance, include elements of a fluidics station, what may be referred to as an autoloader, and scanner 110. The instrument control features may also be capable of receiving information from the one more instruments that could include experiment or instrument status, process steps, or other relevant information. The instrument control features could, for example, be under the control of or an element of the single interface. In the present example, a user may input desired control commands and/or receive the instrument control information via a GUI. Additional examples of instrument control via a GUI or other interface is provided in U.S. Provisional Patent Application Ser. No. 60/483,812, titled "System, Method and Computer Software for Instrument Control, Data Acquisition and Analysis", filed Jun. 30, 2003, which is hereby incorporated by reference herein in its entirety for all purposes.

In some embodiments, image data is operated upon by applications 272 to generate intermediate results. Examples of intermediate results include so-called cell intensity files (*.cel) and chip files (*.chp) generated by Affymetrix® GeneChip® Operating Software or Affymetrix® Microarray Suite (as described, for example, in U.S. patent application Ser. Nos. 10/219,882, and 10/764,663, both of which are hereby incorporated herein by reference in their entireties for all purposes) and spot files (*.spt) generated by Affymetrix® Jaguar™ software (as described, for example, in PCT Application PCT/US 01/26390 and in U.S. patent application Ser. Nos. 09/681,819, 09/682,071, 09/682,074, and 09/682,076, all of which are hereby incorporated by reference herein in their entireties for all purposes). For convenience, the term "file" often is used herein to refer to data generated or used by applications 272 and executable counterparts of other applications, but any of a variety of alternative techniques known in the relevant art for storing, conveying, and/or manipulating data may be employed.

For example, applications 272 receives image data derived from a GeneChip® probe array and generates a cell intensity file. This file contains, for each probe scanned by scanner 110, a single value representative of the intensities of pixels measured by scanner 110 for that probe. Thus, this value is a measure of the abundance of tagged mRNA's present in the target that hybridized to the corresponding probe. Many such mRNA's may be present in each probe, as a probe on a GeneChip® probe array may include, for example, millions of oligonucleotides designed to detect the mRNA's. As noted, another file illustratively assumed to be generated by applications 272 is a chip file. In the present example, in which applications 272 include Affymetrix® GeneChip® Operating Software, the chip file is derived from analysis of the cell file combined in some cases with information derived from lab data and/or library files that specify details regarding the sequences and locations of probes and controls. The resulting data stored in the chip file includes degrees of hybridization, absolute and/or differential (over two or more experiments) expression, genotype comparisons, detection of polymorphisms and mutations, and other analytical results.

In another example, in which applications 272 includes Affymetrix® Jaguar™ software operating on image data from a spotted probe array, the resulting spot file includes the intensities of labeled targets that hybridized to probes in the array. Further details regarding cell files, chip files, and spot files are provided in U.S. patent application Ser. Nos. 09/682,098, 09/682,071, and 10/126,468, incorporated by reference above. As will be appreciated by those skilled in the relevant art, the preceding and following descriptions of files generated by applications 272 are exemplary only, and the data described, and other data, may be processed, combined, arranged, and/or presented in many other ways.

User 100 and/or automated data input devices or programs (not shown) may provide data related to the design or conduct of experiments. As one further non-limiting example related to the processing of an Affymetrix® GeneChip® probe array, the user may specify an Affymetrix catalogue or custom chip type (e.g., Human Genome U133 plus 2.0 chip) either by selecting from a predetermined list presented by GCOS or by scanning a bar code related to a chip to read its type. GCOS may associate the chip type with various scanning parameters stored in data tables including the area of the chip that is to be scanned, the location of chrome borders on the chip used for auto-focusing, the wavelength or intensity of laser light to be used in reading the chip, and so on. As noted, applications 272 may apply some of this data in the generation of intermediate results. For example, information about the dyes may be incorporated into determinations of relative expression.

Those of ordinary skill in the related art will appreciate that one or more operations of applications 272 may be performed by software or firmware associated with various instruments. For example, scanner computer 210 may include a firmware component that performs or controls one or more operations associated with scanner 110.

Figure 3:
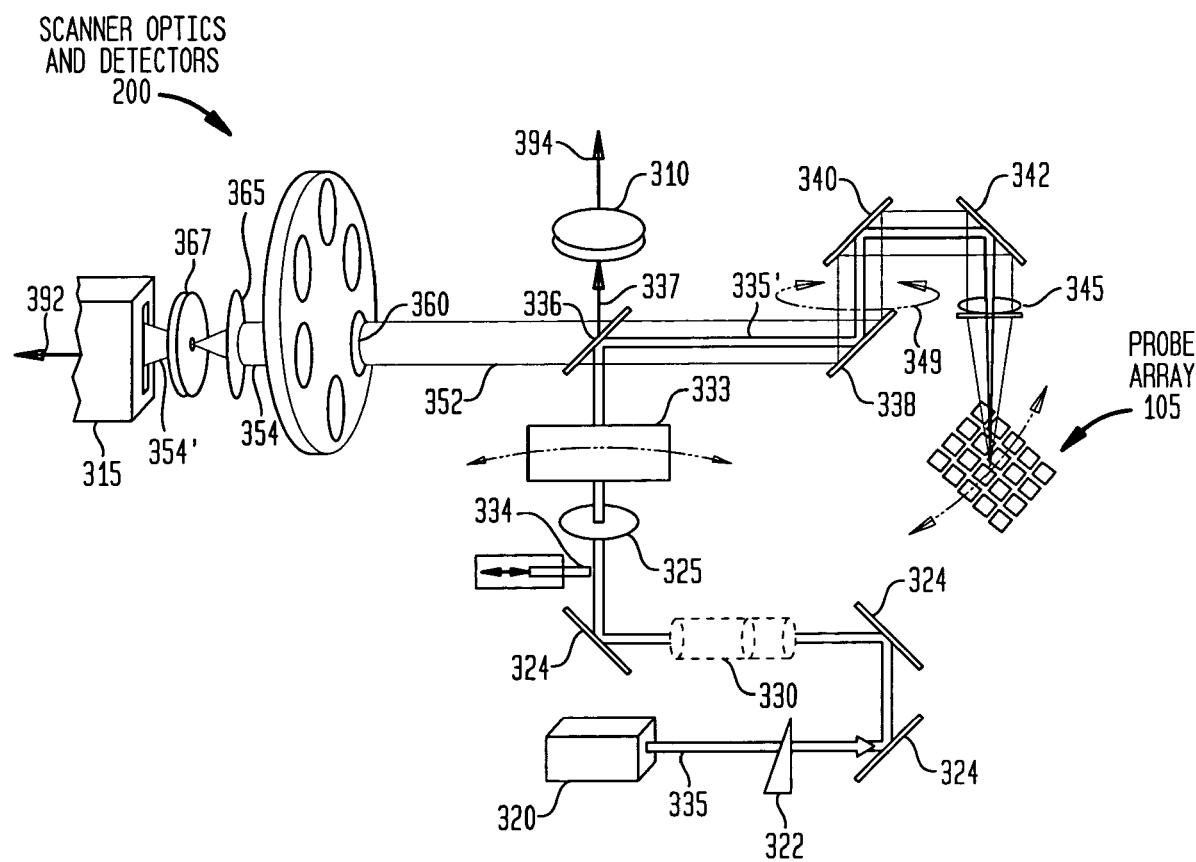
FIG. 3 is a simplified graphical representation of one embodiment of the scanner optics and detectors of FIG. 2 that includes a wavelength tunable source and wavelength tuning elements.

Scanner 110: Labeled targets hybridized to probe arrays may be detected using various devices, sometimes referred to as scanners, as described above with respect to methods and apparatus for signal detection. An illustrative device is shown in FIG. 1 as scanner 110, and in greater detail with exemplary components in FIGS. 2 and 3. For example, scanners image the targets by detecting fluorescent or other emissions from labels associated with target molecules, or by detecting transmitted, reflected, or scattered radiation. A typical scheme employs optical and other elements to provide excitation light and to selectively collect the emissions examples of which are illustrated in FIGS. 2 and 3 as scanner optics and detectors 200.

For example, scanner 110 provides a signal representing the intensities (and possibly other characteristics, such as color) of the detected emissions or reflected wavelengths of light, as well as the locations on the substrate where the emissions or reflected wavelengths were detected. Typically, the signal includes intensity information corresponding to elemental sub-areas of the scanned substrate. The term "elemental" in this context means that the intensities, and/or other characteristics, of the emissions or reflected wavelengths from this area each are represented by a single value. When displayed as an image for viewing or processing, elemental picture elements, or pixels, often represent this information. Thus, in the present example, a pixel may have a single value representing the intensity of the elemental sub-area of the substrate from which the emissions or reflected wavelengths were scanned. The pixel may also have another value representing another characteristic, such as color, positive or negative image, or other type of image representation. The size of a pixel may vary in different embodiments and could include a 2.5 µm, 1.5 µm, 1.0 µm, or sub-micron pixel size. Two examples where the signal may be incorporated into data are data files in the form *.dat or *.tif as generated respectively by Affymetrix® Microarray Suite (described in U.S. patent application Ser. No. 10/219,882, incorporated above) or Affymetrix® GeneChip® Operating Software based on images scanned from GeneChip® arrays, and Affymetrix® Jaguar™ software (described in U.S. patent application Ser. No. 09/682,071, incorporated above) based on images scanned from spotted arrays. Examples of scanner systems that may be implemented with embodiments of the present invention include U.S. patent application Ser. No. 10/389,194, and U.S. Provisional Patent Application Ser. No. 60/493,495 both of which are incorporated by reference above.

Array Transport frame 205: An element of scanner 110 illustrated in FIG. 2 includes array transport frame 205 that provides positional control of probe array 105 when it is received into scanner 110. For example, array transport frame 205 translates probe array 105 in all of the degrees of freedom with respect to a three coordinate system (i.e. X, Y, and Z axes) required for the operations that include autofocus, scanning, and calibration. Those of ordinary skill in the related art will appreciate that the term "degrees of freedom" generally refers to the number of independent parameters required to specify the position and orientation of an object.

Some implementations of array transport frame 205 may include an array holder, pitch and roll mechanisms, a Y-stage, and a focus stage (sometimes referred to as a Z stage). For example, under the control of applications 272 or other instrument control implementation, transport frame 205 may provide positional adjustments to probe array 105 such as, for instance, in the roll and pitch axes with respect to the plane defined by the substrate of probe array 105 to bring all of the features of probe array 105 into the same plane of focus. Similarly, one or more features of probe array 105 may be brought into the plane of focus by adjusting the distance between probe array 105 and objective lens 345 such as by translating probe array 105 using the focus stage to increase or decrease the distance. Additionally, translation of probe array 105 along the Y-axis that sometimes may also be referred to as the "slow" scanning axis may in one embodiment be accomplished by the Y-stage such as by iteratively incrementing some defined distance such as, for instance, a distance that is proportional to pixel or spot size, after a line of pixel data is acquired in what may be referred to as the "fast" scanning axis until all of the data from probe array 105 has been acquired.

Additional examples of array transport mechanisms within microarray scanners are described in U.S. patent application Ser. No. 10/389,194, filed Mar. 14, 2003, incorporated by reference above.

Scanner Optics and Detectors 200: FIG. 3 provides a simplified graphical example of possible embodiments of optical elements associated with scanner 110, illustrated as scanner optics and detectors 200. For example, an element of the presently described invention includes source 320 that could include a laser such as, for instance, a solid state, diode pumped, frequency doubled Nd: YAG (Neodymium-doped Yttrium Aluminum Garnet) or YVO4 laser producing green laser light having a wavelength of 532 nm or other laser implementation. In the present example, source 320 provides light within the excitation range of one or more fluorescent labels associated with target molecules hybridized to probes disposed on probe array 105. Also in the present example, the wavelength of the excitation light provided by source 320 is tunable such to enable the use multiple color assays (i.e. employing multiple fluorescent labels with distinct ranges of excitation and emission wavelengths) associated with an embodiment of probe array 105. Those of ordinary skill in the related art will appreciate that other types of sources 320 may be employed in the present invention such as incandescent sources, one or more light emitting diodes (sometime referred to as LED's), halogen or xenon sources, metal halide sources, or other sources known in the art.

In some embodiments, a single implementation of source 320 is employed that produces a single excitation beam, illustrated in FIG. 3 as excitation beam 335. Alternative embodiments may include multiple implementations of source 320 that each provide excitation light that may be combined into a single beam or directed along separate optical paths to a target, although those of ordinary skill in the related art will appreciate that there are several advantages to implementing a single source over multiple sources such as complexity, space, power, and expense. In each of the embodiments source 320 may include at least one tunable laser to provide a selectable wavelength of light that, for example, may be varied by applications 272 or other software or firmware implementation during a scanning operation or for successive scan operations. In the present example, it may be desirable in some implementations to provide multiple wavelengths of light during the acquisition of each pixel of image data, where the excitation wavelength may be dynamically changed during the pixel acquisition period. Application 272 may process the acquired pixel data and associate each known excitation wavelength during the period with received emissions to produce an unambiguous image of the fluorescent labels present.

In another example, one or more elements or methods may be employed to tune the wavelength of excitation beam 335 produced by source 320 to correspond to the excitation wavelengths of each of multiple fluorophores having a different range of excitation spectra. In the present example, a probe array experiment may comprise the use of two fluorophores that have different excitation wavelength properties, where each excitation wavelength is associated with a particular emission wavelength. Scanner 110 may tune excitation beam 335 to correspond to the excitation wavelength of the first fluorophore, and perform a complete scan. In the present example, excitation beam 335 is then tuned to the excitation wavelength of the second fluorophore and probe array 105 is completely scanned again. The process may be repeated for each fluorophore used in the experiment. Those of ordinary skill in the related art will appreciate that the risk of photobleaching fluorophores is low based, at least in part, upon the degree of difference between excitation spectra associated with each fluorophore. The term "photobleaching" as used herein generally refers to a characteristic of some fluorescent molecules where the amount of emitted light is dependant upon the amount of time that a fluorophore is exposed to the excitation light. The length of time of exposure to the excitation wavelengths corresponds to a reduction in emission intensity from the fluorescent molecule until it is reduced to a value that may be zero.

Those of ordinary skill in the related art will appreciate that a variety of methods exist for tuning the wavelength produced by each source 320. For example, the optical telecom industry has employed what may be referred to as "Dense-Wave Division Multiplexing" techniques have incorporated tunable light sources for highly efficient communication networks such as fiber optic networks.

Some embodiments of tuning excitation beam 335 may include components and/or methods that are internal to source 320. For example, where source 320 includes a laser such as, for instance, what may be referred to as a semiconductor laser diode, the length of the internal cavity path may be dynamically changed, where the change of distance that light travels along the light path changes the wavelength of light produced. In the present example, micro-electronic machines (hereafter referred to as MEMS) may be used to operate mirrors that alter the internal cavity path length based, at least in part, upon the position of the mirror. In the present example, the MEMS may move the mirror under the control of applications 272 to increase or decrease the internal cavity path length to achieve a desired wavelength output from laser 320.

In the same or alternative embodiments, one or more components and/or methods that are external to source 320 may be applied to tune the wavelength of beam 335. For example, illustrated in FIG. 3 is wavelength tuning element 322. Element 322 may include a variety of elements known to those of ordinary skill in the related art for wavelength tuning of laser beams. Element 322 may include what are referred to as wedge etalons, gratings, or other elements commonly used. For example, one or more elements 322 may be used to tune the wavelength of excitation beam 335. In the present example, element 322 could include what may be referred to as a wedge etalon that may be translated by applications 272 or other application in a plane that is normal to the optical path where the translation changes the width of the etalon that beam 335 must pass through. The width of the etalon determines the wavelength of beam 335 that is output from the etalon. The one or more elements 322 may be translated using methods commonly known to those of ordinary skill in the related art.

Further references herein to source 320 generally will assume for illustrative purposes that they are lasers, but, as noted, other types of sources, e.g., x-ray sources, light emitting diodes, incandescent sources, or other electromagnetic sources may be used in various implementations. The Handbook of Biological Confocal Microscopy (James B. Pawley, ed.) (2.ed.; 1995; Plenum Press, NY), includes information known to those of ordinary skill in the art regarding the use of lasers and associated optics, is hereby incorporated herein by reference in its entirety.

FIG. 3 further provides an illustrative example of the paths of excitation beam 335 and emission beam 352 and a plurality of optical components that comprise scanner optics 200. In the present example, excitation beam 335 is emitted from source 320 and is directed along an optical path by one or more turning mirrors 324 toward a three-lens beam conditioner/expander 330. Turning mirrors are commonly associated with optical systems to provide the necessary adjustments to what may be referred to as the optical path such as, for instance, to allow for alignment of excitation beam 335 at objective lens 345 and to allow for alignment of emission beam 354 at detector 315. For example, turning mirrors 324 also serve to "fold" the optical path into a more compact size & shape to facilitate overall scanner packaging. The number of turning mirrors 324 may vary in different embodiments and may depend on the requirements of the optical path. In some embodiments it may be desirable that excitation beam 335 has a known diameter. Beam conditioner/expander 330 may provide one or more optical elements that adjust a beam diameter to a value that could, for instance, include a diameter of 1.076 mm ±10%. For example, the one or more optical elements could include a three-lens beam expander that may increase the diameter of excitation beam 335 to a desired value. Alternatively, the one or more optical elements may reduce the diameter of excitation beam 335 to a desired value. Additionally, the one or more optical elements of beam conditioner/expander 430 may further condition one or more properties of excitation beam 335 to provide other desirable characteristics, such as providing what those of ordinary skill in the related art refer to as a plane wavefront to objective lens 345. Excitation beam 335 with the desirable characteristics may then exit beam conditioner/expander 330 and continue along the optical path that may again be redirected by one or more turning mirrors 324 towards excitation filter 325.

Filter 325 may be used to remove or block light at wavelengths other than excitation wavelengths, and generally need not be included if, for example, source 320 does not produce light at these extraneous wavelengths. However, it may be desirable in some applications to use inexpensive lasers and often it is cheaper to filter out-of-mode laser emissions than to design the laser to avoid producing such extraneous emissions. In some embodiments, filter 325 allows all or a substantial portion of light at one or more excitation wavelengths to pass through without affecting other characteristics of excitation beam 335, such as the desirable characteristics modified by beam conditioner/expander 330. Also, a plurality of filters 325 may also be associated with a filter wheel or other means for selectively translating a desired filter in the optical path. For example, where excitation beam 335 is tunable to a variety of desired wavelengths as described above it may be desirable to translate an implementation of filter 325 into the optical path of excitation bean 335 that is associated with the particular wavelength.

After exiting filter 325 excitation beam 335 may then be directed along the optical path to laser attenuator 333. Laser attenuator 333 may provide a means for adjusting the level of power of excitation beam 335. In some embodiments, attenuator 333 may, for instance, be comprised of a variable neutral density filter. Those of ordinary skill in the related art will appreciate that neutral density filters, such as absorptive, metallic, or other type of neutral density filter, may be used for reducing the amount of light that is allowed to pass through. The amount of light reduction may depend upon what is referred to as the density of the filter, for instance, as the density increases the amount of light allowed to pass through decreases. The neutral density filter may additionally include a density gradient. For example, the presently described embodiment may include laser attenuator 333 that includes a neutral density filter with a density gradient. Attenuator 333, acting under the control of applications 272 may use a step motor that alters the position of the neutral density filter with respect to the optical path. The neutral density filter thus reduces the amount of light allowed to pass through based, at least in part, upon the position of the filter gradient relative to the optical path. In the present example, the power level of excitation beam is measured by laser power monitor 310 that is described further below, and may be dynamically adjusted to a desired level.

Some embodiments may include one or more implementations of shutter 334. Some implementations may include positioning shutter 334 in one or more locations within scanner 110, along the optical path such that shutter 334 provides a means to block all laser light from reaching probe array 105, and in some implementations additionally blocking all laser light from reaching laser power monitor 310. Shutter 334 may use a variety of means to completely block the light beam. For example shutter 334 may use a motor under the control of applications 272 to extend/retract a solid barrier that could be constructed of metal, plastic, or other appropriate material capable of blocking essentially all of the laser light beam, such as excitation beam 335. Shutter 334 may be used for a variety of purposes such as, for example, for blocking all light from one or more photo detectors or monitors, including detector 315 and laser power monitor 310. In the present example, blocking the light may be used for calibration methods that measure and make adjustments to what is referred to as the "dark current" or background noise of the photo detectors.

Components of scanner optics and detectors 200 placed in the optical path after elements such as attenuator 333 and/or shutter 334 may include dichroic beam splitter 336. Those of ordinary skill in the related art will appreciate that a dichroic beam splitter, also commonly referred to as a dichroic mirror, may include an optical element that is highly reflective to light of a certain wavelength range, and allow transmission of light through the beam splitter or mirror at one or more other wavelength ranges. In some embodiments, beam splitter 336 could also include what is referred to as a geometric beam splitter where a portion of the surface of beam splitter 336 is reflective to all light or light within a particular range of wavelengths, and the remaining portion is permissive to the light. Alternatively, the beam splitter or mirror may reflect a certain percentage of light at a particular wavelength and allow transmission of the remaining percentage. For example, dichroic beam splitter 336 may direct most of the excitation beam, illustrated as excitation beam 335', along an optical path towards objective lens 345 while allowing the small fractional portion of excitation beam 335 that is not reflected to pass through beam splitter 336, illustrated in FIG. 3 as partial excitation beam 337 In the present example, partial excitation beam 337 passes through dichroic beam splitter 336 to laser power monitor 310 for the purpose of measuring the power level of excitation beam 335 and providing feedback to applications 272. Applications 272 may then make adjustments, if necessary, to the power level via laser attenuator 333 as described above.

Monitor 310 may be any of a variety of conventional devices for detecting partial excitation beam 337, such as a silicon detector for providing an electrical signal representative of detected light, a photodiode, a charge-coupled device, a photomultiplier tube, or any other detection device for providing a signal indicative of detected light that is now available or that may be developed in the future. As illustrated in FIG. 3, detector 310 generates excitation signal 394 that represents the detected signal from partial excitation beam 337. In accordance with known techniques, the amplitude, phase, or other characteristic of excitation signal 394 is designed to vary in a known or determinable fashion depending on the power of excitation beam 335. The term "power" in this context refers to the capability of beam 335 to evoke emissions. For example, the power of beam 335 typically may be measured in milliwatts of laser energy with respect to the illustrated example in which the laser energy evokes a fluorescent signal. Thus, excitation signal 394 includes values that represent the power of beam 335 during particular times or time periods. Applications 272 may receive signal 394 for evaluation and, as described above, if necessary make adjustments.

After reflection from beam splitter 336, excitation beam 335' may continue along an optical path that is directed via periscope mirror 338, turning mirror 340, and arm end turning mirror 342 to objective lens 345. In the illustrated implementation mirrors 338, 340, and 342 may have the same reflective properties as turning mirrors 324, and could, in some implementations, be used interchangeably with turning mirrors 324.

Lens 345 in the illustrated implementation may include a small, light-weight lens located on the end of an arm that is driven by a galvanometer around an axis perpendicular to the plane represented by galvo rotation 349. In one embodiment, lens 345 focuses excitation beam 335' down to a specified spot size at the best plane of focus that could, for instance, include a 3.5 µm spot size. Galvo rotation 349 results in objective lens 345 moving in an arc over a substrate, providing what may be referred to as an arcuate path that may also be referred to herein as a "scanning line", upon which biological materials typically have been synthesized or have been deposited. The arcuate path may, for instance, move in a 36 degree arc over a substrate. One or more fluorophores associated with the biological materials emit emission beam 352 at characteristic wavelengths in accordance with well-known principles. The term "fluorophore" commonly refers to a molecule that produces fluorescent light by energy transfer from light, chemical, or other types of energy sources.

Emission beam 352 in the illustrated example follows the reverse optical path as described with respect to excitation beam 335 until reaching dichroic beam splitter 336. In accordance with well known techniques and principles, the characteristics of beam splitter 336 are selected so that beam 352 (or a portion of it) passes through the mirror rather than being reflected. Emission beam 352 is then directed along a desired optical path to filter wheel 360.

In one embodiment, filter wheel 360 may be provided to filter out spectral components of emission beam 352 that are outside of the emission band of one or more particular fluorophores. The emission band is determined by the characteristic emission frequencies of those fluorophores that are responsive to the frequency of excitation beam 335. Thus, for example, excitation beam 335 from source 320 excites certain fluorophores to a much greater degree than others.

The result may include filtered emission beam 354 that is a representation of emission beam 352 that has been filtered by a desired filter of filter wheel 360.

In some implementations filter wheel 360 is capable of holding a plurality of filters that each could be tuned to different wavelengths corresponding to the emission spectra from different fluorophores. Filter wheel 360 may include a mechanism for turning the wheel to position a desired filter in the optical path of emission beam 352. The mechanism may include a motor or some other device for turning that may be responsive to instructions from application 272. For example, biological probe array experiments could be carried out on the same probe array where a plurality of fluorophores with different excitation and emission spectra are used that could be excited by a single source with tunable wavelengths or multiple sources. Additionally, multiple fluorescent dyes could be used that have the same excitation wavelengths but have differing emission spectral properties could be produced by methods such as those known to those in the art as fluorescent resonant energy transfer (FRET), or semiconductor nanocrystals (sometimes referred to as Quantum Dots). For example, FRET may be achieved when there are two fluorophores present in the same molecule. The emission wavelength of one fluorophore overlaps the excitation wavelength of the second fluorophore and results in the emission of a wavelength from the second fluorophore that is atypical of the class of fluorophores that use that excitation wavelength. Thus by using an excitation beam of a single wavelength it is possible to obtain distinctly different emissions so that different features of a probe array could be labeled in a single experiment.

For example probe array 105 could be scanned using a filter of one wavelength, then one or more additional scans could be performed that each correspond to a particular fluorophore and filter pair. In the present example, the wavelength of excitation beam 335 from source 320 could be tuned specifically to excite a particular fluorophore. Instrument control and image processing applications 272 could then process the data so that the user could be presented with a single image or other format for data analysis.

In other implementations, multiple excitation sources 320 (or one or more adjustable-wavelength excitation sources) and corresponding multiple optical elements in optical paths similar to the illustrated one could be employed for simultaneous scans at multiple wavelengths. Other examples of scanner systems that utilize multiple emission wavelengths are described in U.S. Pat. No. 6,490,533, titled "System, Method, and Product For Dynamic Noise Reduction in Scanning of Biological Materials", filed Dec. 3, 2001; U.S. Pat. No. 6,650,411, titled "System, Method, and Product for Pixel Clocking in Scanning of Biological Materials", filed Dec. 3, 2001; and U.S. Pat. No. 6,643,015, titled "System, Method, and Product for Symmetrical Filtering in Scanning of Biological Materials", filed Dec. 3, 2001 each of which are hereby incorporated by reference in their entireties for all purposes.

In accordance with techniques well known to those of ordinary skill in the relevant arts, including that of confocal microscopy, beam 354 may be focused by various optical elements such as lens 365 and passed through illustrative pinhole 367, aperture, or other element. In accordance with known techniques, pinhole 367 is positioned such that it rejects light from focal planes other than the plane of focus of objective lens 345 (i.e., out-of-focus light), and thus increases the resolution of resulting images.

In the presently described implementation, pinhole 367 may be bi-directionally moveable along the optical path. As those of ordinary skill in the related art will appreciate, the appropriate placement of pinhole 367 to reject out of focus light is dependant upon the wavelength of emitted beam 354. Pinhole 367 may be movable via a motor or other means under the control of applications 272 to a position that corresponds to the emission wavelength of the fluorophore being scanned. In the same or alternative embodiments, pinhole 367 may comprise a sufficiently large diameter to accommodate the emission wavelengths of several fluorophores if those wavelengths are relatively similar to each other. Also, some embodiments of pinhole 367 may include an "iris" type of aperture that expands and contracts so that the diameter of the hole or aperture is sufficient to permit the desired wavelength of light at the plane of focus to pass through while rejecting light that is substantially out of focus.

Alternatively, a series of pinholes 367 may be utilized. For example, there may be an implementation of pinhole 367 associated with each fluorophore used with a biological probe array. Each implementation of pinhole 367 may be placed in the appropriate position to reject out of focus light corresponding to the emission wavelength of its associated fluorophore. Each of pinholes 367 may be mounted on a translatable stage, rotatable axis, or other means to move pinhole 367 in and out of the optical path. In the present example, the implementation of pinhole 367 corresponding to the fluorophore being scanned is positioned in the optical path under the control of executables 372 and/or 272, while the other implementations of pinhole 367 are positioned outside of the optical path thus allowing the implementation of pinhole 367 in the optical path to reject out of focus light.

After passing through pinhole 367, the portion of filtered emission beam 354 that corresponds to the plane of focus, represented as filtered emission beam 354', continues along a desired optical path and impinges upon detector 315.

Similar to excitation detector 310, emission detector 415 may be a silicon detector for providing an electrical signal representative of detected light, or it may be a photodiode, a charge-coupled device, a photomultiplier tube, or any other detection device that is now available or that may be developed in the future for providing a signal indicative of detected light. Detector 315 generates signal 392 that represents filtered emission beam 354' in the manner noted above with respect to the generation of excitation signal 394 by detector 310. Signal 392 and excitation signal 394 may be provided to applications 272 for processing, as previously described.

Figure 4:
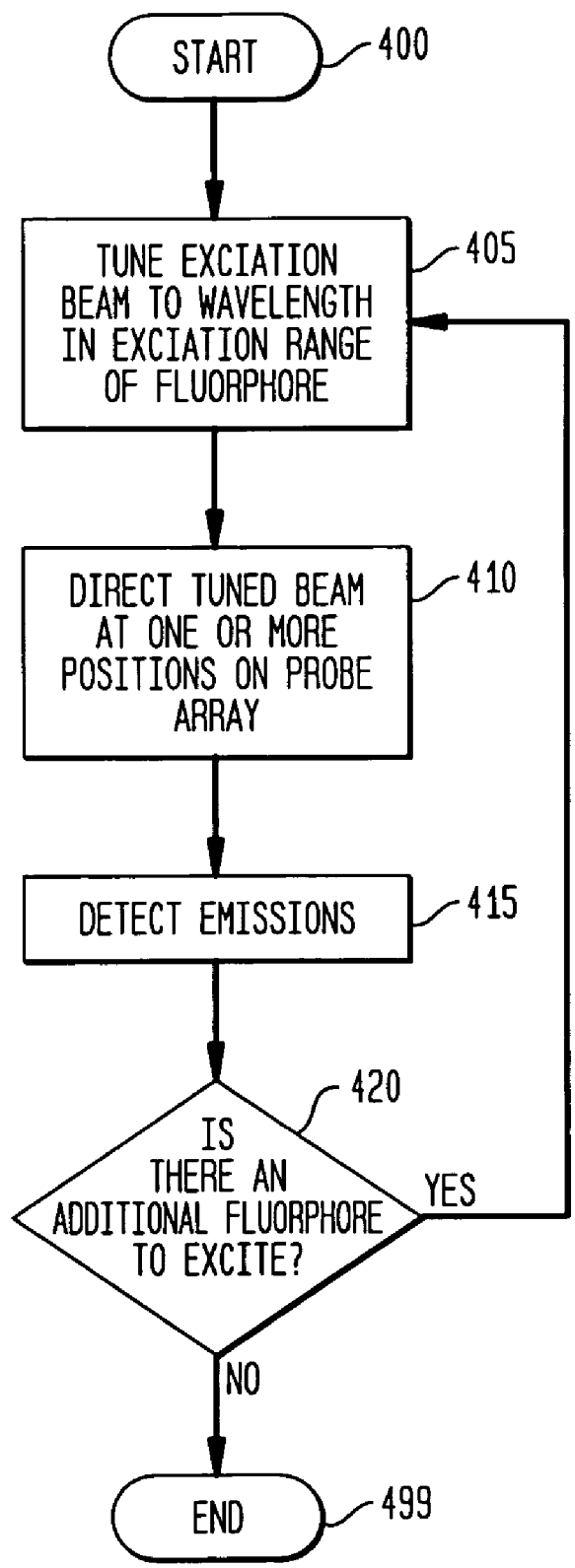
FIG. 4 is a functional block diagram of one embodiment of a method of tuning an excitation beam, directing the beam at one or more positions associated with a probe array, and detecting the emissions.

FIG. 4 provides an illustrative example of a method for employing a tunable excitation beam with an assay that includes multiple fluorescent labels or fluorophores, such as, for instance a four color assay that may be desirable for use in certain genotyping applications where each color may be associated with a particular nucleotide i.e. A, G, C, or T. As illustrated in step 405, excitation beam 335 may be tuned by a variety of methods as described above to a particular wavelength that is within the excitation range of one or more fluorophores. The tuned beam is then directed at one or more positions on probe array 105, illustrated in step 410, using the components of optics 200 as described above. The directing of step 410 and subsequent collecting step 415 may include directing the beam at a single pixel position, one or more lines of pixels that may for instance be defined by the scanning line as described above, or all pixel positions associated with probe array 105 and detecting the emissions associated with the fluorescent label at each pixel position if present. Decision element 420 illustrates whether there is another fluorescent label with a different excitation range to be scanned, where in the example of a 4 color assay there may be 4 excitation ranges needed for 4 labels. If necessary to scan another fluorescent label, the method is repeated from step 405 where the beam is tuned to the appropriate wavelength. If the wavelengths associated with all fluorescent labels in the assay have been scanned, the method is finished. Again, the method may be performed iteratively for each pixel position, one or more lines of pixels, or performed a single time for an entire array of pixel positions.

Having described various embodiments and implementations, it should be apparent to those skilled in the relevant art that the foregoing is illustrative only and not limiting, having been presented by way of example only. Many other schemes for distributing functions among the various functional elements of the illustrated embodiment are possible. The functions of any element may be carried out in various ways in alternative embodiments.

Also, the functions of several elements may, in alternative embodiments, be carried out by fewer, or a single, element. Similarly, in some embodiments, any functional element may perform fewer, or different, operations than those described with respect to the illustrated embodiment. Also, functional elements shown as distinct for purposes of illustration may be incorporated within other functional elements in a particular implementation. Also, the sequencing of functions or portions of functions generally may be altered. Certain functional elements, files, data structures, and so on may be described in the illustrated embodiments as located in system memory of a particular computer. In other embodiments, however, they may be located on, or distributed across, computer systems or other platforms that are co-located and/or remote from each other. For example, any one or more of data files or data structures described as co-located on and "local" to a server or other computer may be located in a computer system or systems remote from the server. In addition, it will be understood by those skilled in the relevant art that control and data flows between and among functional elements and various data structures may vary in many ways from the control and data flows described above or in documents incorporated by reference herein. More particularly, intermediary functional elements may direct control or data flows, and the functions of various elements may be combined, divided, or otherwise rearranged to allow parallel processing or for other reasons. Also, intermediate data structures or files may be used and various described data structures or files may be combined or otherwise arranged. Numerous other embodiments, and modifications thereof, are contemplated as falling within the scope of the present invention as defined by appended claims and equivalents thereto.

What is claimed is:

1. A system for providing multiple wavelengths of light to a probe array, comprising:
    a source to alternately tune an excitation light to a first wavelength within an excitation range of a first fluorescent label associated with a first target molecule, and a second wavelength within an excitation range of a second fluorescent label associated with a second target molecule, wherein the source alternates between tuning the excitation light to the first and second wavelengths in succession;
    one or more optical elements to direct the excitation light comprising the first wavelength and the excitation light comprising the second wavelength to at least one pixel position associated with the probe array; and
    a detector to detect a third wavelength of light emitted in response to the first wavelength and a fourth wavelength of light emitted in response to the second wavelength.

2. The system of claim 1, wherein:
    the one or more optical elements directs the excitation light comprising the first wavelength and the excitation light comprising the second wavelength at a line comprising a plurality of pixel positions associated with the probe array.

3. The system of claim 1, wherein:
    the one or more optical elements directs the excitation light comprising the first wavelength and the excitation light comprising the second wavelength at all pixel positions associated with the probe array.

4. The system of claim 1, wherein:
    the first target molecule hybridizes a first probe disposed on the probe array, and the second target molecule hybridizes a second probe disposed on the probe array.

5. The system of claim 1, wherein:
    the fiat and second target molecules comprise molecules selected from the group consisting of DNA, RNA, PNA and Protein molecules.

6. The system of claim 1, further comprising:
    generating an image comprising a plurality pixels, wherein one or more of the pixels are representative of the detected third and fourth wavelengths.

7. The system of claim 6, wherein:
    each of the pixels corresponds to a particular pixel position associated with the probe array.

8. The system of claim 1, wherein:
    the source comprises a tunable laser, wherein the laser is tuned by adjusting a distance associated with an internal path length.

9. A system for providing multiple wavelengths of light to a probe array, comprising:
    a source to alternately tune an excitation light to a first wavelength within an excitation range of a first fluorescent label associated with a first target molecule, and a second wavelength within an excitation range of a second fluorescent label associated with a second target molecule, wherein the source alternates between tuning the excitation light to the first and second wavelengths in succession;
    one or more optical elements to direct the first and second wavelengths of light at a probe array;
    a detector to detect a third wavelength of light emitted in response to the first wavelength and a fourth wavelength of light emitted in response to the second wavelength; and
    a computer having executable code stored thereon, wherein the executable code is enabled to generate an image comprising a plurality pixels, wherein one or more of the pixels are representative of the detected third and fourth wavelengths.

10. A method for providing multiple wavelengths of light to a probe array, comprising:
    (a) alternately tuning a source to provide an excitation light of a first wavelength within an excitation range of a first fluorescent label associated with a first target molecule, and a second wavelength within an excitation range of a second fluorescent label associated with a second target molecule, wherein the source alternates between tuning the excitation light to the first and second wavelengths in succession;
    (b) directing the excitation light comprising the first wavelength and the excitation light comprising the second wavelength to at least one pixel position associated with the probe array; and (c) detecting a third wavelength of light emitted in response to the first wavelength and a fourth wavelength of light emitted in response to the second wavelength.

11. The method of claim 10, wherein:

directing the excitation light comprising the first wavelength and the excitation light comprising the second wavelength to at a line comprising a plurality of pixel positions associated with the probe array.

12. The method of claim 10, wherein:

directing the excitation light comprising the first wavelength and the excitation light comprising the second wavelength to at all pixel positions associated with the probe array.

13. The method of claim 10, further comprising:

(d) repeating steps (a) through (c) until each of a plurality of pixel positions associated with the probe array has been scanned.

14. The method of claim 13, further comprising:

(e) generating an image comprising a plurality pixels, wherein one or more of the pixels are representative of the detected third and fourth wavelengths.

15. The method of claim 14, wherein:

each of the pixels corresponds to a particular pixel position associated with the probe array.

16. The method of claim 10, wherein:

the first set of target molecules hybridizes a first set of probes disposed on the probe array, and the second set of target molecules hybridizes a second set of probes disposed on the probe array.

17. The method of claim 10, wherein:

the first and second sets of target molecules comprises one or more molecules selected from the group consisting of DNA, RNA, PNA and Protein molecules.

18. The method of claim 10, wherein:

the source comprises a tunable laser, wherein the laser is tuned by adjusting a distance associated with an internal path length.

* * * * *